(12) United States Patent
Nagano et al.

(10) Patent No.: US 8,376,950 B2
(45) Date of Patent: *Feb. 19, 2013

(54) ULTRASONIC ENDOSCOPE AND ULTRASONIC ENDOSCOPIC APPARATUS

(75) Inventors: Kazuhiko Nagano, Ashigarakami-gun (JP); Hiroaki Hyuga, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 859 days.

This patent is subject to a terminal disclaimer.

(21) Appl. No.: 12/127,884

(22) Filed: May 28, 2008

(65) Prior Publication Data

US 2008/0300492 A1  Dec. 4, 2008

(30) Foreign Application Priority Data

May 31, 2007  (JP) ................................. 2007-145246

(51) Int. Cl.
*A61B 8/00* (2006.01)
(52) U.S. Cl. ........................................ 600/459; 600/462
(58) Field of Classification Search .................. 600/459, 600/462, 466
See application file for complete search history.

(56) References Cited

U.S. PATENT DOCUMENTS

| | | | | |
|---|---|---|---|---|
| 5,402,793 A | * | 4/1995 | Gruner et al. | 600/447 |
| 5,560,362 A | * | 10/1996 | Sliwa et al. | 600/439 |
| 5,961,465 A | * | 10/1999 | Kelly et al. | 600/459 |
| 7,052,463 B2 | * | 5/2006 | Peszynski et al. | 600/459 |
| 7,308,828 B2 | * | 12/2007 | Hashimoto | 73/617 |
| 2005/0075573 A1 | * | 4/2005 | Park et al. | 600/459 |

FOREIGN PATENT DOCUMENTS

| | | |
|---|---|---|
| JP | 9294744 A | 11/1997 |
| JP | 1156763 A | 3/1999 |
| JP | 3061292 U | 6/1999 |
| JP | 11299775 A | 11/1999 |
| JP | 200187262 A | 4/2001 |
| JP | 2006-204552 A | 8/2006 |
| WO | 2006033281 A1 | 3/2006 |

OTHER PUBLICATIONS

Japanese Office Action corresponding to Japanese Patent Application No. 2007-145246, dated Dec. 20, 2011.

* cited by examiner

*Primary Examiner* — Peter Luong
(74) *Attorney, Agent, or Firm* — Sughrue Mion, PLLC

(57) ABSTRACT

An ultrasonic endoscope having a small size and a slight temperature rise of an insertion part even when the transmission output of an ultrasonic transducer part is increased or an imaging device is attached thereto. The ultrasonic endoscope includes: an ultrasonic transducer part having plural ultrasonic transducers for transmitting and receiving ultrasonic waves; a flexing part for flexibly supporting the ultrasonic transducer part; a coupling part for coupling the flexing part to an operation part; a covering material for covering at least the flexing part and the coupling part; and a heat-conducting member provided inside of the covering material and coupled to the ultrasonic transducer part, for transferring heat generated in the ultrasonic transducer part to the operation part.

11 Claims, 7 Drawing Sheets

FIG.3
(a)
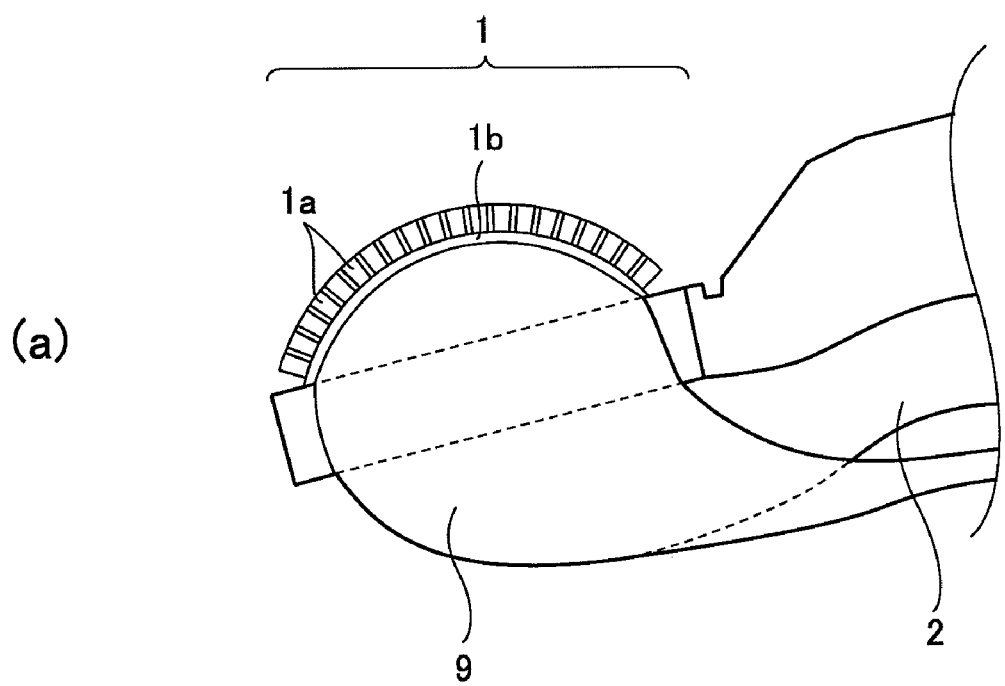
(b)
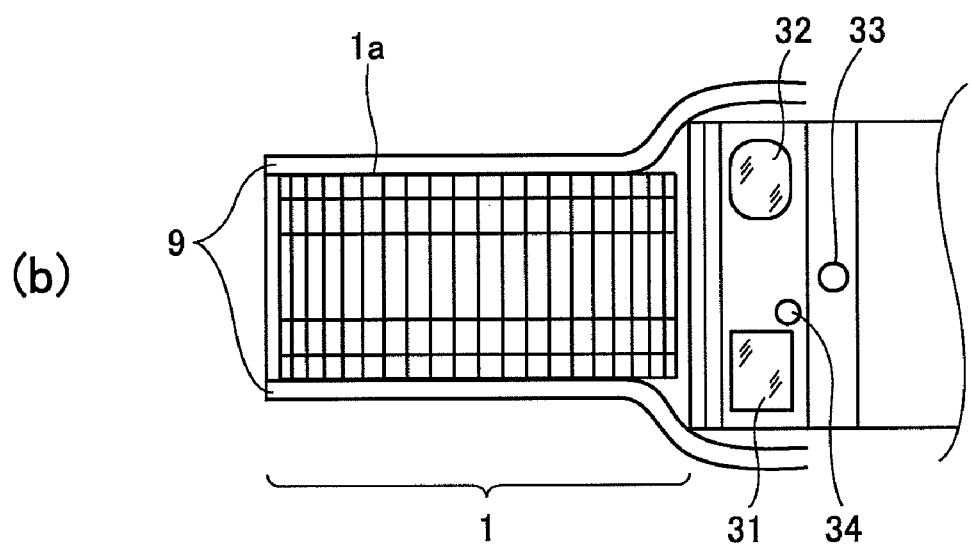

ULTRASONIC ENDOSCOPE AND ULTRASONIC ENDOSCOPIC APPARATUS

BACKGROUND OF THE INVENTION

1. Field of the Invention

The present invention relates to an ultrasonic endoscope to be used for body cavity examination of upper digestive organs, bronchial tube, and so on, and the present invention further relates to an ultrasonic endoscopic apparatus including the ultrasonic endoscope.

2. Description of a Related Art

In medical fields, various imaging technologies have been developed in order to observe the interior of an object to be inspected and make diagnoses. Among them, especially, ultrasonic imaging for acquiring interior information of the object by transmitting and receiving ultrasonic waves enables image observation in real time and provides no exposure to radiation unlike other medical image technologies such as X-ray photography or RI (radio isotope) scintillation camera. Accordingly, ultrasonic imaging is utilized as an imaging technology at a high level of safety in a wide range of departments including not only the fetal diagnosis in the obstetrics, but also gynecology, circulatory system, digestive system, etc.

The ultrasonic imaging is an image generation technology utilizing the nature of ultrasonic waves that the ultrasonic waves are reflected at a boundary between regions with different acoustic impedances (e.g., a boundary between structures). Typically, an ultrasonic diagnostic apparatus is provided with a body surface ultrasonic probe to be used in contact with the object or intracavity ultrasonic probe to be used by being inserted into a body cavity of the object. Further, in recent years, an ultrasonic endoscope in combination of an endoscope for optically observing the interior of the object and an ultrasonic probe for intracavity has been used.

Ultrasonic beams are transmitted toward the object such as a human body and ultrasonic echoes generated in the object are received by using the ultrasonic endoscope, and thereby, ultrasonic image information is acquired. On the basis of the ultrasonic image information, ultrasonic images of structures (e.g., internal organs, diseased tissues, or the like) existing within the object are displayed on a display unit of an ultrasonic endoscopic apparatus main body connected to the ultrasonic endoscope.

As an ultrasonic transducer for transmitting and receiving ultrasonic waves, a vibrator (piezoelectric vibrator) having electrodes formed on both sides of a material that expresses a piezoelectric property (a piezoelectric material) is generally used. As the piezoelectric material, piezoelectric ceramics represented by PZT (Pb (lead) zirconate titanate), a polymeric piezoelectric material represented by PVDF (polyvinylidene difluoride), or the like is used.

When a voltage is applied to the electrodes of the vibrator, the piezoelectric material expands and contracts due to the piezoelectric effect and generates ultrasonic waves. Accordingly, plural vibrators are one-dimensionally or two-dimensionally arranged and the vibrators are sequentially driven, and thereby, an ultrasonic beam to be transmitted in a desired direction can be formed. Further, the vibrators expand and contract by receiving propagating ultrasonic waves and generate electric signals. These electric signals are used as reception signals of the ultrasonic waves.

When ultrasonic waves are transmitted, drive signals having great energy are supplied to the ultrasonic transducers. In this regard, not the entire energy of the drive signals is converted into acoustic energy but a significant proportion of the energy becomes heat, and there has been a problem that the temperature rises in use of the ultrasonic endoscope. However, the insertion part of the ultrasonic endoscope is used in direct contact with the living body such as a human body, and a request that the surface temperature of the insertion part of the ultrasonic endoscope is controlled to a predetermined temperature or less has been made for safety reasons of preventing low-temperature burn and so on.

As a related technology, Japanese Patent Application Publication JP-P2006-204552A discloses an ultrasonic probe in which the heat generated in a vibrator part and a circuit board is transferred to a shield case via a heat-conducting part, and the heat transferred to the shield case is absorbed by a heat absorbing part including a refrigerant feeder and a refrigerant pipe for cooling the vibrator part. However, a small-diameter endoscope such as a bronchial endoscope having an outer diameter of φ6.9 mm or less has no space for such a heat absorbing part including a refrigerant feeder and a refrigerant pipe.

Further, Japanese Registered Utility Model JP-Z-3061292 discloses that a heat transfer structure in contact with an integrated circuit within an ultrasonic transducer for extracting heat generated there to the outside is provided, and the extracted heat by the heat transfer structure is transferred to a conducting material that functions as a heat sink within a communication cable. However, the signal cable of the endoscope has a small sectional area, and, if the signal cable is used for heat dissipation, no sufficient heat dissipation effect is obtained due to the small sectional area.

In an ultrasonic endoscope to be used by being inserted into a body cavity of a patient, in order to reduce the physical stress on the patient to be examined, it is desired that the diameter of the insertion part is made smaller. Specifically, in body cavity examination of upper digestive organs, bronchial tube, and so on, a small-diameter endoscope having an outer diameter of φ6.9 mm is used, and downsizing of the ultrasonic endoscope becomes a challenge in view of reduction in physical stress on patients.

Further, in the ultrasonic endoscope, stacking the ultrasonic transducers to raise reception sensitivity is being considered for an improvement in diagnostic accuracy. However, as the transmission output of ultrasonic waves is increased by stacking the ultrasonic transducers, the amount of heat released from the ultrasonic transducers becomes larger. According to the structure of a conventional ultrasonic endoscope, if the transmission output of ultrasonic waves is increased by stacking the ultrasonic transducers, there is a problem that the temperature of the insertion part in contact with the inner wall of the body cavity rises due to the heat generation of the ultrasonic transducers. With downsizing of the ultrasonic endoscope, the temperature rise of the insertion part due to heat generation of the ultrasonic transducers has become an increasingly serious problem, and the problem is an issue to be solved.

Furthermore, when an imaging device (CCD or the like) and a light guide are attached to the insertion part of the ultrasonic endoscope, a problem of temperature rise in the insertion part due to heat generation from the imaging device and the light guide exit part arises, and the problem is an issue to be solved.

SUMMARY OF THE INVENTION

The present invention has been achieved in view of the above-mentioned problems. A purpose of the present invention is to provide an ultrasonic endoscope having a small size and a slight temperature rise of an insertion part even when the transmission output of an ultrasonic transducer part is increased or an imaging device is attached thereto, and an ultrasonic endoscopic apparatus including the ultrasonic endoscope.

In order to accomplish the purpose, an ultrasonic endoscope according to one aspect of the present invention includes: an ultrasonic transducer part having plural ultrasonic transducers for transmitting and receiving ultrasonic waves; a flexing part for flexibly supporting the ultrasonic transducer part; a coupling part for coupling the flexing part to an operation part; a covering material for covering at least the flexing part and the coupling part; and a heat-conducting member provided inside of the covering material and coupled to the ultrasonic transducer part, for transferring heat generated in the ultrasonic transducer part to the operation part.

Further, an ultrasonic endoscopic apparatus according to one aspect of the present invention includes: an ultrasonic endoscope according to the present invention, and an ultrasonic endoscopic apparatus main body for processing signals from the ultrasonic endoscope to display ultrasonic images and including a cooing device for cooling the heat-conducting member.

According to the present invention, since the heat-conducting member is provided inside of the covering material that covers the insertion part of the ultrasonic endoscope, an ultrasonic endoscope having a small size and a slight temperature rise of an insertion part even when the transmission output of an ultrasonic transducer part is increased or an imaging device is attached thereto can be provided.

BRIEF DESCRIPTION OF THE DRAWINGS

FIG. 3 shows a configuration around an ultrasonic transducer part in the insertion part of the ultrasonic endoscope shown in FIG. 2;

DESCRIPTION OF THE PREFERRED EMBODIMENTS

Hereinafter, embodiments of the present invention will be explained in detail with reference to the drawings. The same reference numbers will be assigned to the same component elements and the description thereof will be omitted.

Figure 1:
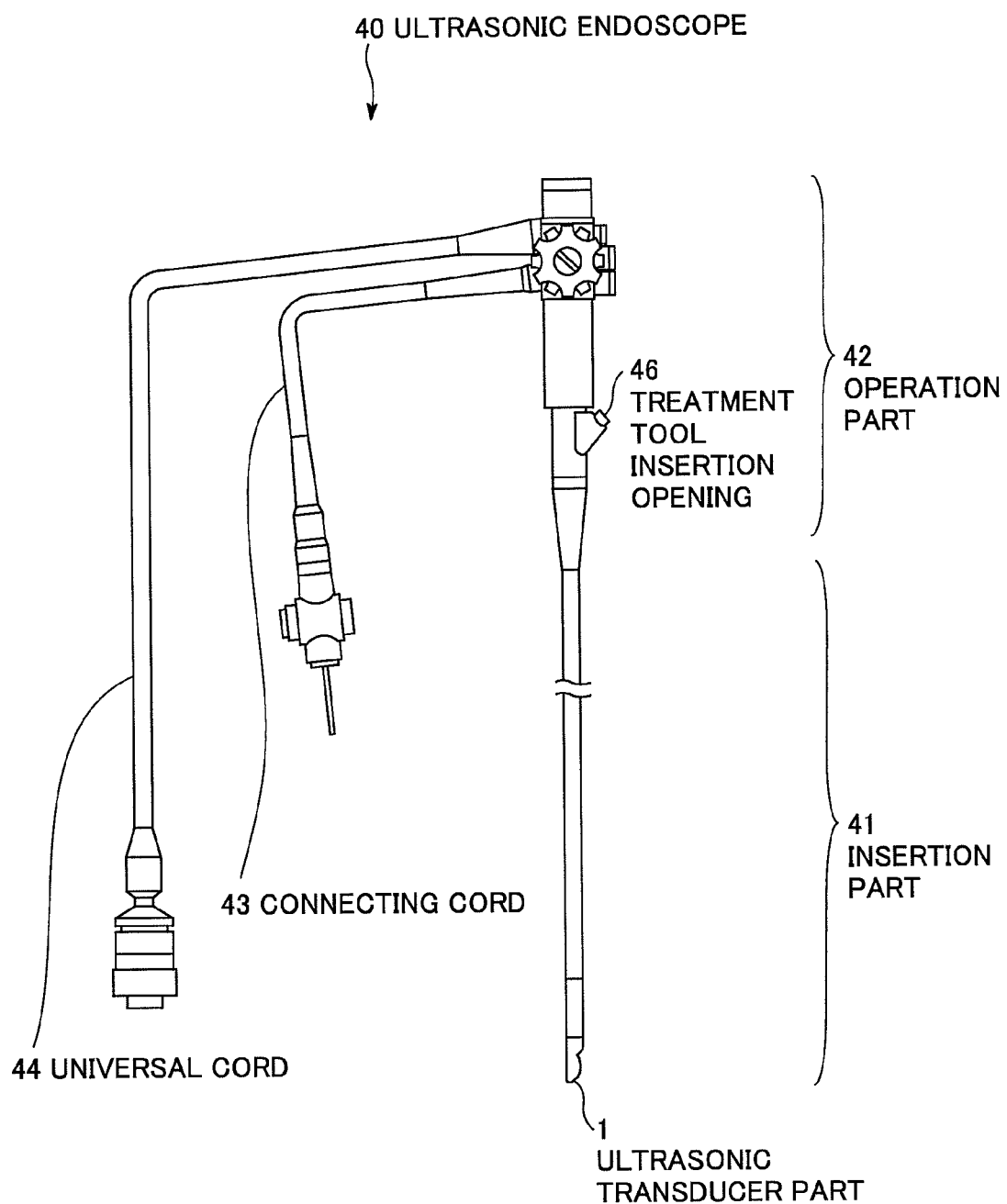
FIG. 1 is a schematic diagram showing an appearance of an ultrasonic endoscope according to the respective embodiments of the present invention.

FIG. 1 is a schematic diagram showing an appearance of an ultrasonic endoscope according to the respective embodiments of the present invention. As shown in FIG. 1, an ultrasonic endoscope 40 includes an insertion part 41, an operation part 42, a connecting cord 43, and a universal cord 44. The insertion part 41 includes an elongated tube formed of a member having flexibility so as to be inserted into a body of an object to be inspected, and an ultrasonic transducer part 1 at the leading end thereof.

The operation part 42 is provided at the base end of the insertion part 41 and connected to an ultrasonic endoscopic apparatus main body via the connecting cord 43 and the universal cord 44. A treatment tool insertion opening 46 provided in the operation part 42 is a hole for leading in a treatment tool such as a punctuation needle or forceps. Various treatments are performed within a body cavity of the object by operating it with the operation part 42.

Figure 2:
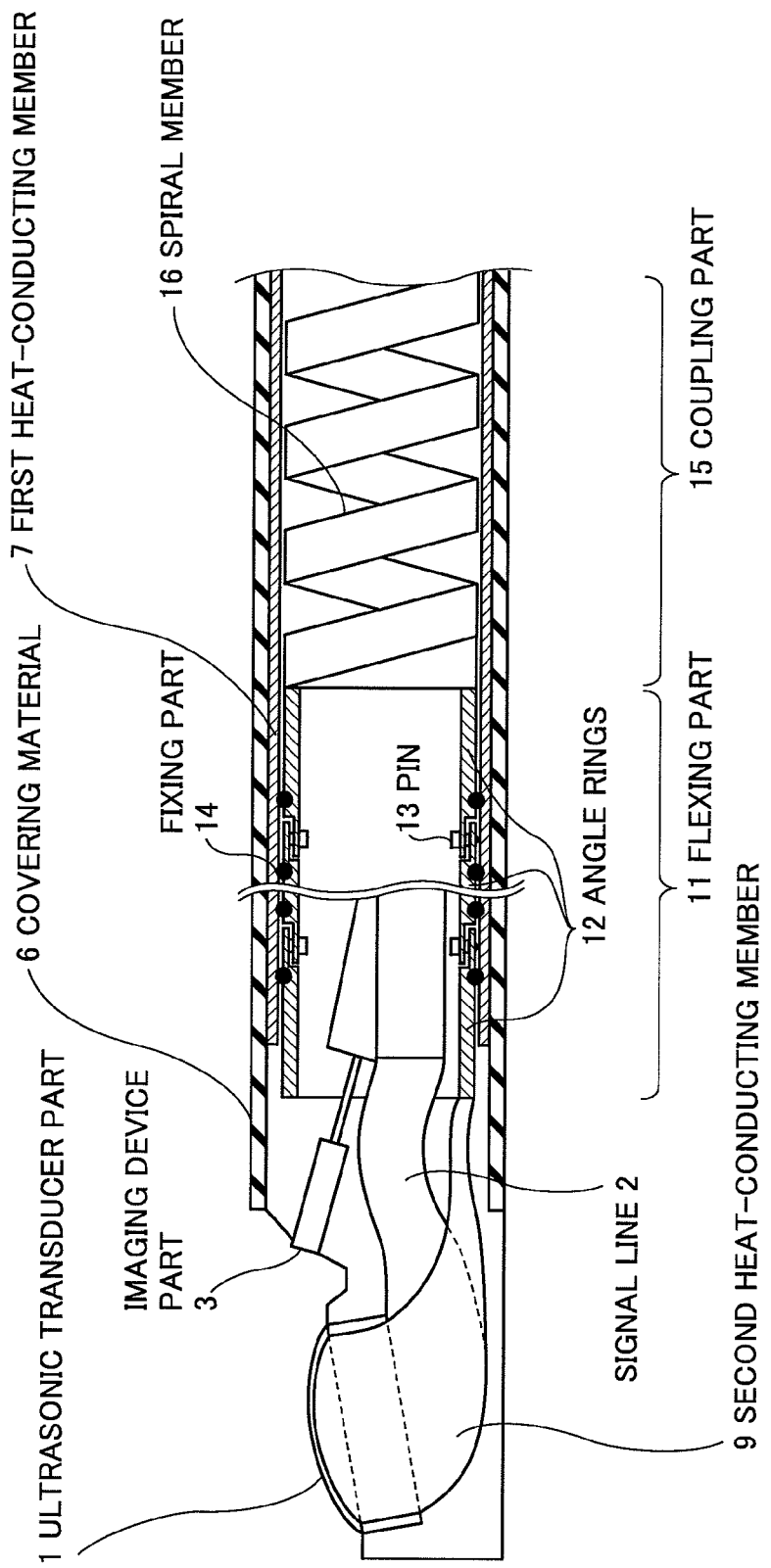
FIG. 2 shows a leading end of the ultrasonic endoscope according to the first embodiment of the present invention.

FIG. 2 shows the leading end of the insertion part of the ultrasonic endoscope according to the first embodiment of the present invention. As shown in FIG. 2, the leading end of the insertion part of the ultrasonic endoscope according to the first embodiment of the present invention has an ultrasonic transducer part 1 for transmitting and receiving ultrasonic waves, a signal line 2 for transmitting signals between the ultrasonic transducer part 1 and the ultrasonic endoscope main body, an imaging device part 3 for optically imaging affected parts, a flexing part 11 for flexibly supporting the ultrasonic transducer part 1 and the imaging device part 3, a coupling part 15 for coupling the flexing part 11 to the operation part 42 (FIG. 1), and a covering material 6 for covering at least the flexing part 11 and the coupling part 15.

The ultrasonic transducer part 1 has 64 ultrasonic transducers arranged on a backing material, for example. The signal line 2 includes plural shield lines connected to the 64 ultrasonic transducers, respectively, for example. The flexing part 11 includes plural angle rings 12 connected to one another to be relatively displaced by pins 13. The coupling part 15 includes a spiral member 16. The spiral member 16 is generally formed of stainless steel, but, in the embodiment, preferably formed of copper or copper alloy in view of heat release. The covering material 6 is formed of an insulating material of fluorine-containing rubber, for example.

In the ultrasonic endoscope according to the embodiment, at least in the flexing part 11 and the coupling part 15, a first heat-conducting member 7 is provided inside of the covering material 6. The first heat-conducting member 7 may be extended to a part of the operation part 42 (FIG. 1). The first heat-conducting member 7 has high heat conductivity and flexibility and durability to bending, and is formed in a foil, wire, mesh, or sheet shape by employing a material containing metal and/or graphite. Preferably, the metal material contains copper or copper alloy with good heat conductivity. Thereby, heat is released from the leading end of the insertion part 41 (FIG. 1) toward the operation part 42. Further, since the first heat-conducting member 7 is provided inside of the covering material 6 so as to contact the covering material 6, heat is also released to the outside air via the covering material 6. As a result, the heat release from the ultrasonic transducer part 1 and/or the imaging device part 3 to the outside is promoted.

Further, it is preferable that the first heat-conducting member 7 is insulated from the ground line of the ultrasonic endoscope main body in order to reduce the inductive noise from the ultrasonic endoscope main body. In the embodiment, no shield layer is provided inside of the covering material 6 in order to reduce the diameter of the insertion part of the ultrasonic endoscope.

Furthermore, in the ultrasonic endoscope of the embodiment, a second heat-conducting member 9 is provided in order to reduce the thermal resistance between the ultrasonic transducer part 1 and the first heat-conducting member 7. The second heat-conducting member 9 is formed in a foil, wire, mesh, or sheet shape by employing a material containing metal and/or graphite, to have a thickness of 30 μm to several hundreds of micrometers, for example. Preferably, the metal material contains copper or copper alloy with good heat conductivity. Since the second heat-conducting member 9 is formed in a thin layer, the ultrasonic transducer part 1 and the second heat-conducting member 9 can be accommodated within the small-diameter endoscope tube.

One end of the second heat-conducting member 9 is connected to the side surface of the ultrasonic transducer part 1. The other end of the second heat-conducting member 9 may be connected to the first heat-conducting member 7 such that the heat generated in the ultrasonic transducer part 1 may be transferred to the first heat-conducting member 7 via the second heat-conducting member 9. Alternatively, as described below, the other end of the second heat-conducting member 9 may be connected to the angle rings 12 in contact with the first heat-conducting member 7 such that the heat generated in the ultrasonic transducer part 1 may be transferred from the second heat-conducting member 9 further to the first heat-conducting member 7 via the angle rings 12 of the flexing part 11.

The flexing part 11 is provided near the leading end of the endoscope, for example. The flexing part 11 is configured by arranging support points for curving the plural top-like angle rings 12 with displacement of 90° with respect to each other in a staggered manner. Those angle rings 12 are connected to one another to be relatively displaced by using pins 13 and form a hinge structure. A wire is provided inside of the angle rings 12, and the entire flexing part 11 bends and operates like joints. Preferably, the angle rings 12 are formed of a high heat-conducting material such as copper or copper alloy.

However, in the part of the pins 13 connecting the plural angle rings 12, heat is conducted via the pins 13 and sufficient heat release is hardly achieved. On this account, in the embodiment, the respective angle rings 12 are fixed to the first heat-conducting member 7 having flexibility by using fixing parts 14, and heat is released to the first heat-conducting member 7 via the fixing parts 14. For example, the fixing parts 14 are fixed by soldering or the like.

FIG. 3 shows a configuration around the ultrasonic transducer part in the insertion part of the ultrasonic endoscope shown in FIG. 2. FIG. 3(*a*) is a side view of the periphery of the ultrasonic transducer part, and FIG. 3(*b*) is a plan view of the periphery of the ultrasonic transducer part.

As shown in FIG. 3(*b*), in the insertion part of the ultrasonic endoscope, the ultrasonic transducer part 1, an observation window 31, an illumination window 32, a treatment tool passage opening 33, and a nozzle hole 34 are provided. In FIG. 3(*b*), an objective lens is fit in the observation window 31, and a solid-state image sensor such as a CCD camera or an input end of an image guide is arranged at the imaging position of the objective lens. These configure an observation optics. Further, an illumination lens for outputting illumination light to be supplied from the light source unit via a light guide is fit in the illumination window 32. These configure an illumination optics.

The treatment tool passage opening 33 is a hole for leading out a treatment tool or the like. Various treatments are performed within a body cavity of the object by projecting the treatment tool such as the punctuation needle or forceps (not shown) from the hole. The nozzle hole 34 is provided for injecting a liquid (water or the like) for cleaning the observation window 31 and the illumination window 32.

The ultrasonic transducer part 1 is, for example, a convex-type multirow array and includes plural ultrasonic transducers 1*a* arranged in five rows and a backing material 1*b* on which those ultrasonic transducers 1*a* are arranged. The second heat-conducting member 9 may be joined to the side surface of the backing material 1*b*. Alternatively, the second heat-conducting member 9 may be joined to the side surface of the backing material 1*b* of the ultrasonic transducer part 1 and the side surfaces of the plural ultrasonic transducers 1*a*. In this case, it is necessary to insulate the individual electrodes of the ultrasonic transducers 1*a* from the second heat-conducting member 9 by employing an insulating film. A common electrode of the ultrasonic transducers 1*a* may be connected to the second heat-conducting member 9 or insulated from the second heat-conducting member 9.

Figure 4:
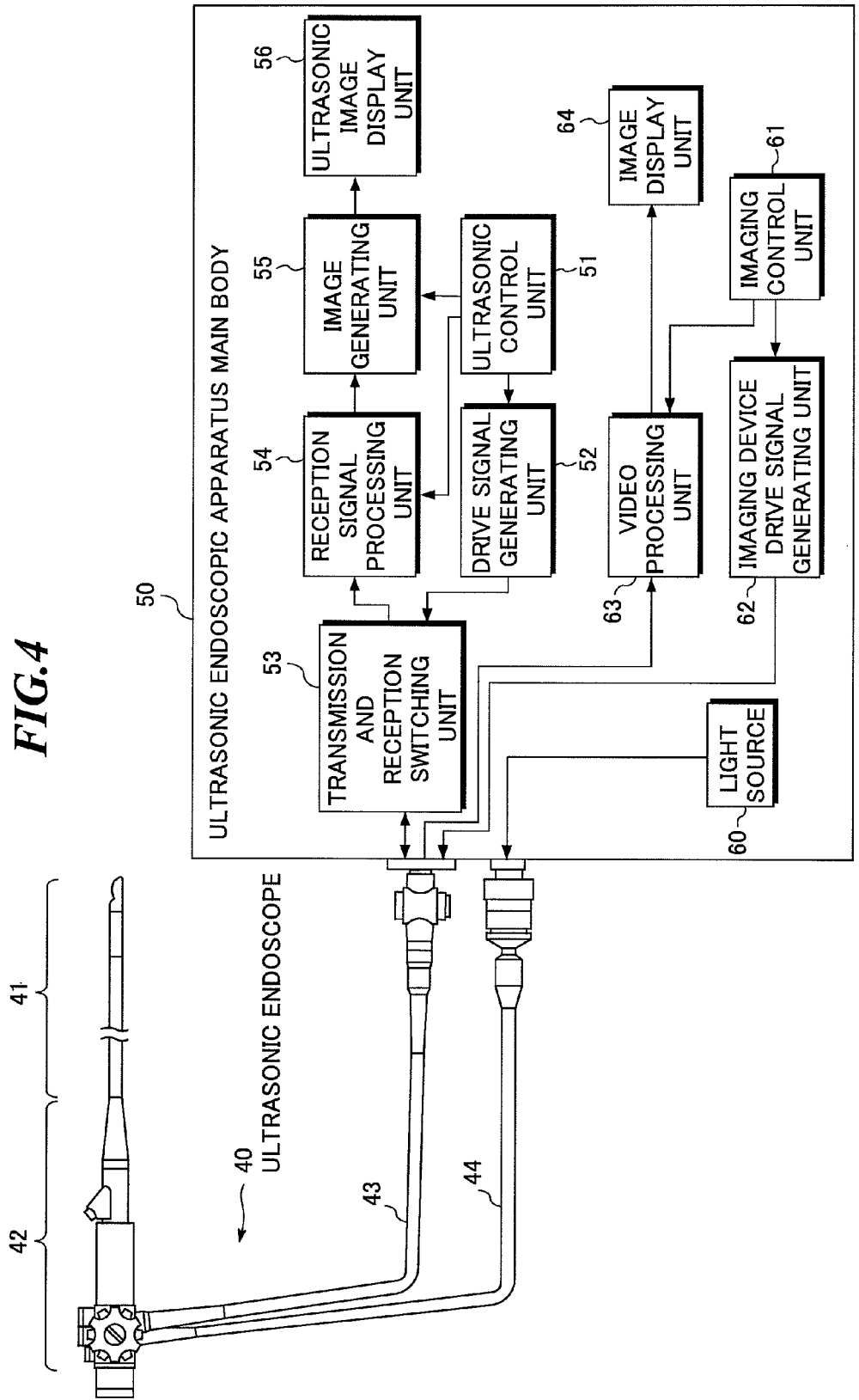
FIG. 4 shows an ultrasonic endoscopic apparatus including the ultrasonic endoscope according to the respective embodiments of the present invention and the ultrasonic endoscopic apparatus main body.

FIG. 4 shows an ultrasonic endoscopic apparatus including the ultrasonic endoscope according to the respective embodiments of the present invention and an ultrasonic endoscopic apparatus main body. The plural ultrasonic transducers included in the ultrasonic transducer part 1 (FIG. 2) are electrically connected to the ultrasonic endoscopic apparatus main body 50 by using plural shield lines via the insertion part 41, the operation part 42, and the connecting cord 43. Those shield lines transmit plural drive signals generated in the ultrasonic endoscopic apparatus main body 50 to the respective ultrasonic transducers and transmit plural reception signals outputted from the respective ultrasonic transducers to the ultrasonic endoscopic apparatus main body 50.

The ultrasonic endoscopic apparatus main body 50 includes an ultrasonic control unit 51, a drive signal generating unit 52, a transmission and reception switching unit 53, a reception signal processing unit 54, an image generating unit 55, an ultrasonic image display unit 56, a light source 60, an imaging control unit 61, an imaging device drive signal generating unit 62, a video processing unit 63, and an image display unit 64.

The ultrasonic control unit 51 controls imaging operation using the ultrasonic transducer part 1. The drive signal generating unit 52 includes plural drive circuits (pulsers or the like), for example, and generates plural drive signals to be used for respectively driving the plural ultrasonic transducers. The transmission and reception switching unit 53 switches between output of the drive signals to the ultrasonic transducer part 1 and input of the reception signals from the ultrasonic transducer part 1.

The reception signal processing unit 54 includes plural preamplifiers, plural A/D converters, a digital signal processing circuit or CPU, for example, and performs predetermined signal processing such as amplification, adjusting phases and addition, and detection on the reception signals outputted from the plural ultrasonic transducers. The image generating unit 55 generates image data representing ultrasonic images based on the reception signals on which the predetermined signal processing has been performed. The ultrasonic image display unit 56 displays ultrasonic images based on the image data generated in this manner.

The light source 60 emits light to be used for illumination of the object. The light outputted from the light source 60 illuminates the object via the universal cord 44 and through the illumination window 32 (FIG. 3(*b*)) of the insertion part 41. The illuminated object is imaged by the imaging device part 3 through the observation window 31 (FIG. 3(*b*)) of the insertion part 41, and a video signal outputted from the imaging device part 3 is inputted to the video processing unit 63 of the ultrasonic endoscopic apparatus main body 50 via the connecting cord 43.

The imaging control unit 61 controls imaging operation using the imaging device part 3. The imaging device drive signal generating unit 62 generates drive signals to be supplied to the imaging device part 3. The video processing unit 63 generates image data based on the video signals to be inputted from the imaging device part 3. The image display unit 64 inputs the image data from the video processing unit 63 and displays images of the object.

Next, the second embodiment of the present invention will be explained.

Figure 5:
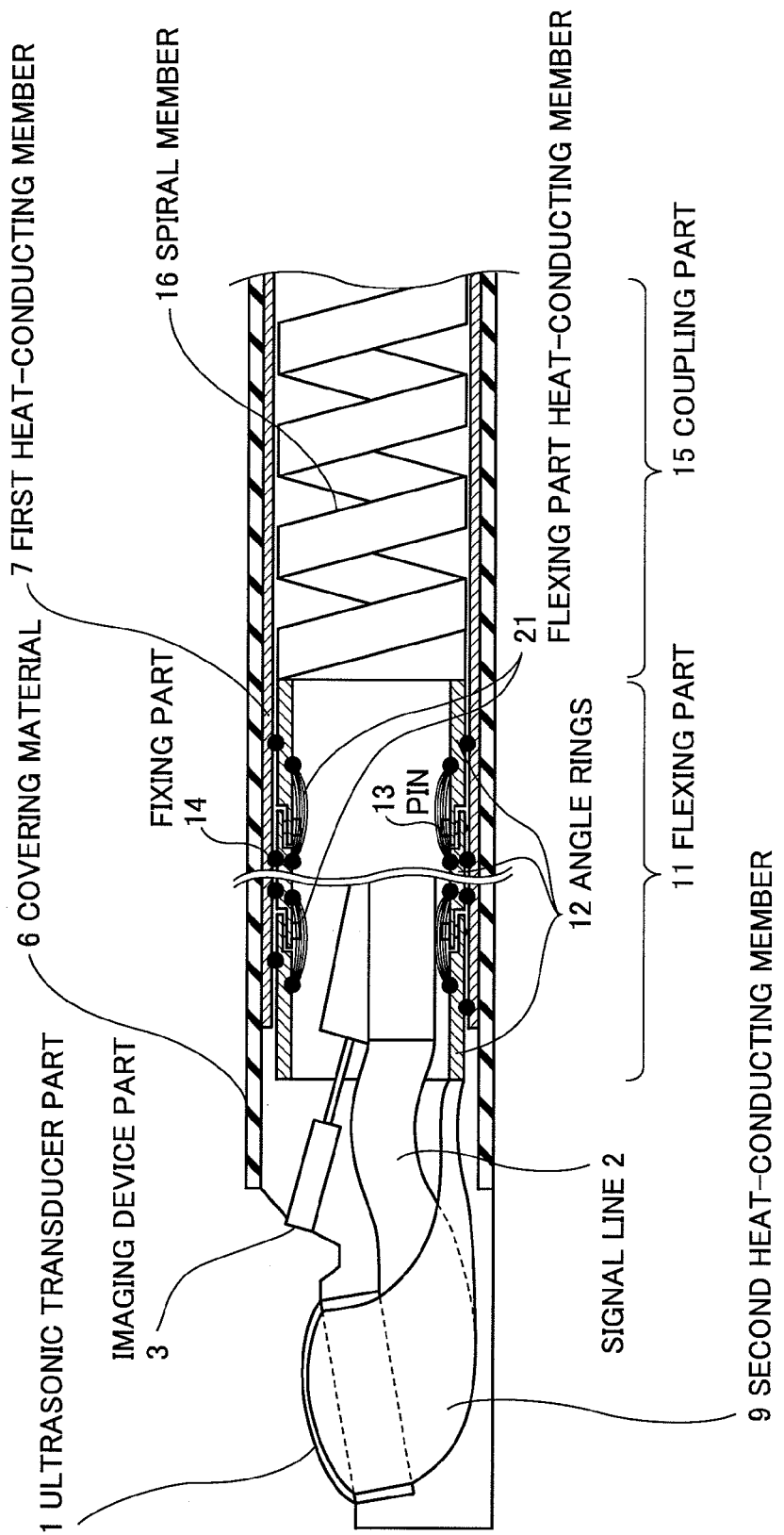
FIG. 5 shows a leading end of an ultrasonic endoscope according to the second embodiment of the present invention.

FIG. 5 schematically shows a leading end of an insertion part of an ultrasonic endoscope according to the second embodiment of the present invention. In the second embodiment of the present invention, the plural angle rings 12 of the flexing part 11 are connected by using the pins 13 as is the case of the first embodiment of the present invention, but sufficient heat release is hardly achieved through the connection by the pins 13. On this account, heat is released from the plural angle rings 12 to the first heat-conducting member 7 via the fixing parts 14 and a flexing part heat-conducting member 21 is provided for promotion of heat transfer among the angle rings 12.

The flexing part heat-conducting member 21 has flexibility and high conductivity, and formed in a foil, wire, mesh, or sheet shape by employing a material containing metal and/or graphite. Preferably, the metal material contains copper or copper alloy with good heat conductivity. According to the second embodiment, since heat is transferred among the plural rings 12 via the flexing part heat-conducting member 21, the heat is released to the first heat-conducting member 7 more efficiently than in the case of the first embodiment.

Next, the third embodiment of the present invention will be explained.

Figure 6:
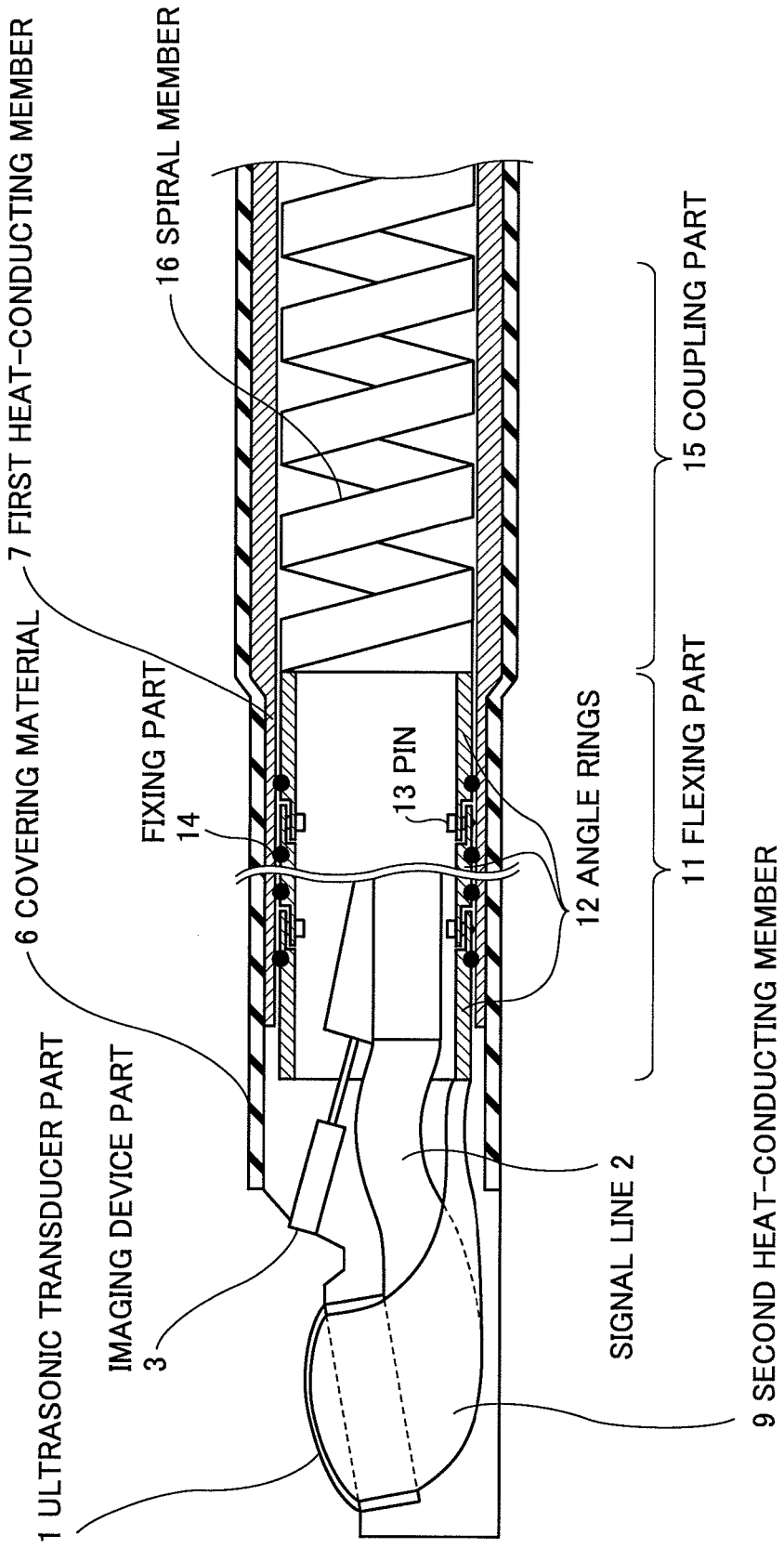
FIG. 6 shows a leading end of an ultrasonic endoscope according to the third embodiment of the present invention.

FIG. 6 schematically shows a leading end of an insertion part of an ultrasonic endoscope according to the third embodiment of the present invention. In the third embodiment of the present invention, the outer diameter of a portion from the ultrasonic transducer part 1 to the flexing part 11 is made smaller than the outer diameter of a portion from the coupling part 15, which is nearer the operation part 42 (FIG. 1) side than the flexing part 11, to the operation part 42. Here, the flexing part 11 is not gradually thin but uniformly thin, and thus, its insertability into thin bronchial tubes is good. Further, the sectional area of the first heat-conducting member 7 at the coupling part 15 is made larger than the sectional area of the first heat-conducting member 7 at the flexing part 11. Thereby, heat radiation of the coupling part 15, which becomes insufficient when the ultrasonic transducers are stacked for increasing the transmission output of ultrasonic waves, is improved and both the greater output and the heat radiation can be achieved.

Next, the fourth embodiment of the present invention will be explained.

Figure 7:
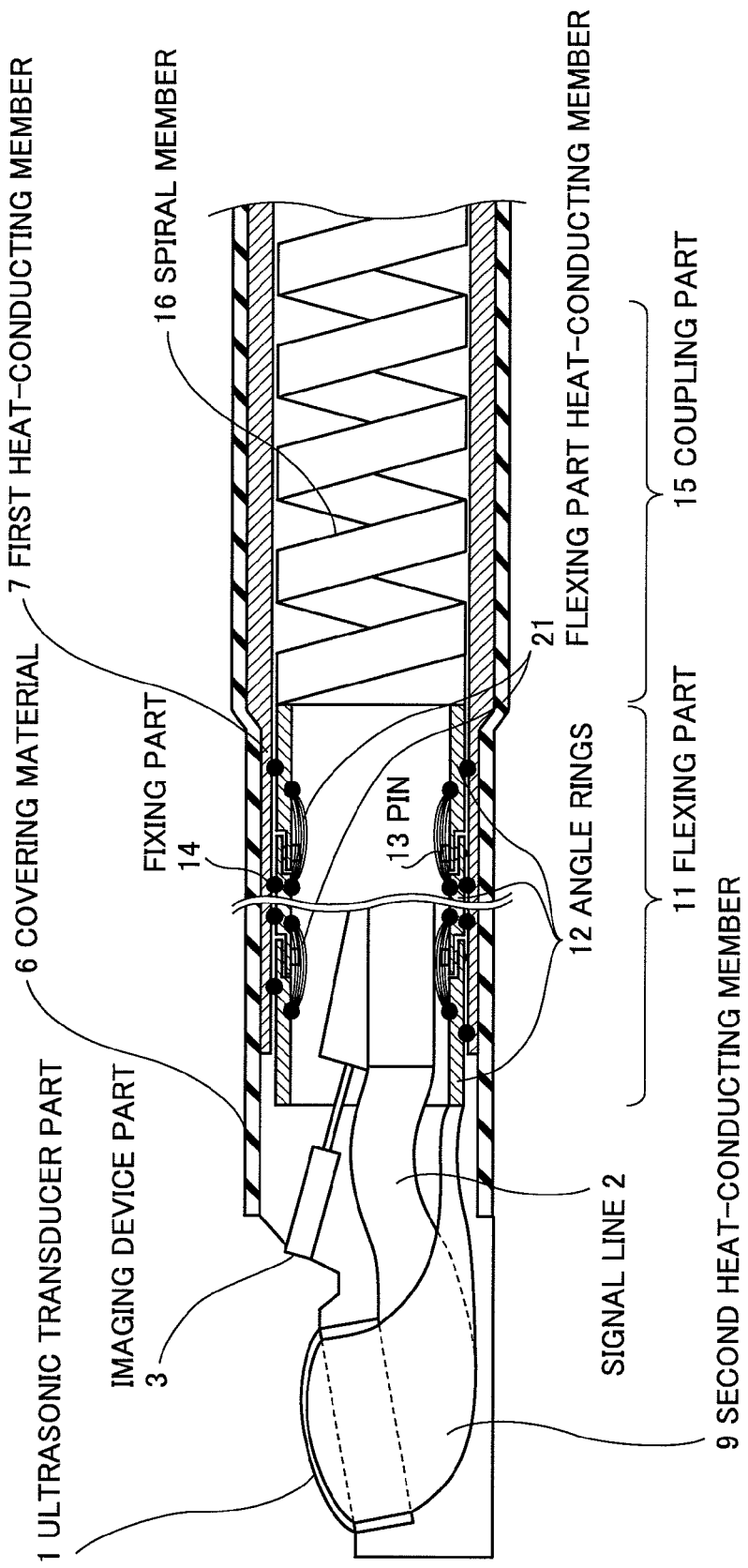
FIG. 7 shows a leading end of an ultrasonic endoscope according to the fourth embodiment of the present invention.

FIG. 7 schematically shows a leading end of an insertion part of an ultrasonic endoscope according to the fourth embodiment of the present invention. In the fourth embodiment of the present invention, the flexing part heat-conducting member 21, which has been explained in the second embodiment of the present invention, is added to the third embodiment of the present invention. According to the fourth embodiment, since heat is transferred among the plural rings 12 via the flexing part heat-conducting member 21, the heat is released to the first heat-conducting member 7 more efficiently than in the case of the third embodiment.

The invention claimed is:

1. An ultrasonic endoscope to be used when connected to an ultrasonic endoscopic apparatus main body, said ultrasonic endoscope comprising:
   an ultrasonic transducer part having plural ultrasonic transducers configured to transmit and receive ultrasonic waves;
   a flexing part that is flexible and configured to support said ultrasonic transducer part;
   an operation part configured to be connected to said ultrasonic endoscopic apparatus main body via at least one cord;
   a coupling part configured to couple said flexing part to said operation part;
   a covering material configured to cover at least said flexing part and said coupling part;
   a first heat-conducting member having one of a foil shape, a wire shape, a mesh shape, and a sheet shape, and provided inside of said covering material and extended to a part of said operation part while being in contact with said covering material to transfer heat generated in said ultrasonic transducer part to said operation part;
   plural angle rings configured of a high heat-conducting material, plural fixing parts configured to fix said plural angle rings to said first heat-conducting member, and plural pins configured to connect said plural angle rings to one another to be relatively displaced; and
   a second heat-conducting member having one end directly fixed to a side surface of the ultrasonic transducer part, and the other end directly fixed to one of said plural angle rings, said second heat-conducting member transferring the heat generated in said ultrasonic transducer part to said first heat-conducting member via said plural angle rings and said plural fixing parts.

2. The ultrasonic endoscope according to claim 1, further comprising:
   an imaging device part that optically images an object to be inspected.

3. The ultrasonic endoscope according to claim 1, wherein said first heat-conducting member contains at least one of metal and graphite.

4. The ultrasonic endoscope according to claim 1, wherein said second heat-conducting member contains at least one of metal and graphite.

5. The ultrasonic endoscope according to claim 1, further comprising:
   a third heat-conducting member connected between adjacent two angle rings.

6. The ultrasonic endoscope according to claim 5, wherein said third heat-conducting member contains at least one of metal and graphite.

7. The ultrasonic endoscope according to claim 1, wherein an outer diameter of a portion from said ultrasonic transducer part to said flexing part is smaller than an outer diameter of a portion from said coupling part to said operation part.

8. The ultrasonic endoscope according to claim 1, wherein a sectional area of said first heat-conducting member at said coupling part is larger than a sectional area of said first heat-conducting member at said flexing part.

9. The ultrasonic endoscope according to claim 1, wherein said second heat-conducting member has one of a foil shape, a wire shape, a mesh shape, and a sheet shape.

10. An ultrasonic endoscopic apparatus including an ultrasonic endoscope and an ultrasonic endoscopic apparatus main body that processes signals from said ultrasonic endoscope to display an ultrasonic image, said ultrasonic endoscope comprising:
    an ultrasonic transducer part having plural ultrasonic transducers configured to transmit and receive ultrasonic waves;
    a flexing part that is flexible and configured to support said ultrasonic transducer part;
    an operation part connected to said ultrasonic endoscopic apparatus main body via at least one cord;

a coupling part configured to couple said flexing part to said operation part;

a covering material configured to cover at least said flexing part and said coupling part; and a first heat-conducting member having one of a foil shape, a wire shape, a mesh shape, and a sheet shape, and provided inside of said covering material and extended to a part of said operation part while being in contact with said covering material to transfer heat generated in said ultrasonic transducer part to said operation part;

plural angle rings configured of a high heat-conducting material, plural fixing parts configured to fix said plural angle rings to said first heat-conducting member, and plural pins configured to connect said plural angle rings to one another to be relatively displaced; and a second heat-conducting member having one end directly fixed to a side surface of the ultrasonic transducer part, and the other end directly fixed to one of said plural angle rings, said second heat-conducting member transferring the heat generated in said ultrasonic transducer part to said first heat-conducting member via said plural angle rings and said plural fixing parts.

11. The ultrasonic endoscopic apparatus according to claim 10, wherein said second heat-conducting member has one of a foil shape, a wire shape, a mesh shape, and a sheet shape.

* * * * *